US00PP17950P2

(12) United States Plant Patent
Rendall

(10) Patent No.: US PP17,950 P2
(45) Date of Patent: Aug. 28, 2007

(54) ***GERANIUM* PLANT NAMED 'TANYA RENDALL'**

(50) Latin Name: *Geranium hybrida*
Varietal Denomination: Tanya Rendall

(75) Inventor: Richard Rendall, Kerkwall Orkney (GB)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 11/245,379

(22) Filed: Oct. 6, 2005

(51) Int. Cl.
*A01H 5/00* (2006.01)

(52) U.S. Cl. ..... Plt./324

(58) Field of Classification Search ..... Plt./324
See application file for complete search history.

(56) References Cited

PUBLICATIONS

GTITM UPOVROM Citation for 'Tanya Rendall' as per QZ PBR 20030238; Apr. 7, 2003.*

* cited by examiner

*Primary Examiner*—Kent Bell
(74) *Attorney, Agent, or Firm*—C. A. Whealy

(57) ABSTRACT

A new and distinct cultivar of *Geranium* plant named 'Tanya Rendall', characterized by its outwardly spreading, trailing and mounded plant habit; brown-colored foliage; freely and uniformly flowering habit; long flowering period; purple violet-colored flowers; and excellent garden performance.

1 Drawing Sheet

Botanical designation: *Geranium hybrida.*
Cultivar denomination: 'Tanya Rendall'.

CROSS-REFERENCE TO RELATED APPLICATIONS

The present application is co-pending with the following related application:

Geranium plant named, 'Luscious Linda', U.S. Plant Patent Application Ser. No. 11/245,298 Applicant Richard Rendall.

BACKGROUND OF THE INVENTION

The present Invention relates to a new and distinct cultivar of *Geranium* plant, botanically known as *Geranium hybrida,* and hereinafter referred to by the cultivar name Tanya Rendall.

The new *Geranium* is a product of a planned breeding program conducted by the Inventor in Kirkwall Orkney, Scotland, United Kingdom. The objective of the breeding program was to create new freely flowering *Geranium* cultivars that have a long flowering period and are suitable for hanging basket and garden use.

The new *Geranium* originated from a cross-pollination in 1998 of the *Geranium hybrida* cultivar Black Ice, not patented, as the female, or seed, parent with an unnamed selection of *Geranium oxonianum* hybrid, not patented, as the male, or pollen, parent. The new *Geranium* was discovered and selected by the Inventor in 2000 as a single flowering plant from within the resultant progeny of the stated cross-pollination in a controlled environment in Kirkwall Orkney, Scotland, United Kingdom.

Asexual reproduction of the new cultivar by divisions in Kirkwall, Orkney, Scotland, United Kingdom since 2002, has shown that the unique features of this new *Geranium* are stable and reproduced true to type in successive generations.

SUMMARY OF THE INVENTION

Plants of the cultivar Tanya Rendall have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Tanya Rendall'. These characteristics in combination distinguish 'Tanya Rendall' as a new and distinct cultivar:

1. Outwardly spreading, trailing and mounded plant habit.
2. Freely and uniformly flowering habit.
3. Brown-colored foliage.
4. Long flowering period.
5. Purple violet-colored flowers.
6. Excellent garden performance.

Compared to plants of the parents, plants of the new *Geranium* have a more mounded plant habit. In addition, plants of the new *Geranium* and the parents differ in foliage and flower coloration as plants of the parents have green-colored leaves and pink-colored flowers.

Plants of the new *Geranium* can be compared to plants of the cultivar Luscious Linda, U.S. Plant patent application Ser. No. 11/245,298. In side-by-side comparisons conducted in Hillegom, The Netherlands, plants of the new *Geranium* differed from plants of the cultivar Luscious Linda in the following characteristics:

1. Plants of the new *Geranium* were larger than plants of the cultivar Luscious Linda.
2. Plants of the new *Geranium* had brown-colored foliage whereas plants of the cultivar Luscious Linda had green-colored foliage.
3. Plants of the new *Geranium* and the cultivar Luscious Linda differed slightly in flower coloration.

Plants of the new *Geranium* can also be compared to plants of the cultivar Dusky Crug, not patented. In side-by-side comparisons conducted by the Inventor in Kirkwall, Orkney, Scotland, United Kingdom, plants of the new *Geranium* differed from plants of the cultivar Dusky Crug in the following characteristics:

1. Plants of the new *Geranium* had a more trailing and mounded plant habit than plants of the cultivar Dusky Crug.
2. Plants of the new *Geranium* and the cultivar Dusky Crug differed in foliage and flower color as plants of the cultivar Dusky Crug have green-colored leaves and creamy white-colored flowers.

BRIEF DESCRIPTION OF THE PHOTOGRAPH

The accompanying colored photograph illustrates the overall appearance of the new *Geranium,* showing the colors as true as it is reasonably possible to obtain in colored reproductions of this type. Colors in the photograph may differ slightly from the color values cited in the detailed botanical description which accurately describe the colors of the new *Geranium.* The photograph comprises a side perspective view of a typical one-year old flowering plant of 'Tanya Rendall' grown in a hanging basket container.

DETAILED BOTANICAL DESCRIPTION

In the following description, color references are made to The Royal Horticultural Society Colour Chart, 1995 Edition, except where general terms of ordinary dictionary significance are used. Plants used for the following description were about one year old and grown in 20-cm hanging basket containers under outdoor field conditions which closely approximate commercial production conditions during the summer in Hillegom, The Netherlands. During the production of the plants, day temperatures ranged from 5° C. to 25° C. and night temperatures ranged from 2° C. to 12° C.

Botanical classification: *Geranium hybrida* cultivar Tanya Rendall.

Parentage:

*Female, or seed, parent.*—*Geranium hybrida* cultivar Black Ice, not patented.

*Male, or pollen, parent.*—Unnamed selection of *Geranium oxonianum* hybrid, not patented.

Propagation:

*Type.*—By divisions.

*Time to initiate roots, summer.*—About three weeks at 18° C.

*Time to initiate roots, winter.*—About five weeks at 18° C.

*Time to produce a rooted young plant, summer.*—About four weeks at 18° C.

*Time to produce a rooted young plant, winter.*—About six weeks at 18° C.

*Rooting habit.*—Freely branching.

Plant description:

*Plant form and habit.*—Perennial flowering plant; outwardly spreading, trailing and mounded growth habit.

*Plant height.*—About 20 cm to 30 cm.

*Plant diameter.*—About 40 cm to 75 cm.

*Lateral branch description.*—Length: About 100 cm. Diameter: About 1 mm. Texture: Pubescent. Color: 148B.

*Foliage description.*—Arrangement: Opposite; simple. Length: About 4 cm to 6 cm. Width: About 6 cm to 8 cm. Shape: Roughly orbicular; seven-lobed, each lobe with three shallow secondary lobes. Apex: Acute. Base: Cordate. Margin: Lobed. Texture, upper surface: Sparsely pubescent. Texture, lower surface: Pubescent. Venation pattern: Palmate; reticulate. Petiole: Length: About 8 cm to 25 cm. Diameter: About 2 mm to 3 mm. Texture, upper and lower surfaces: Pubescent. Color: Developing and fully expanded foliage, upper surface: 166A; towards the margin, 61B. Developing and fully expanded foliage, lower surface: 148A; towards the margin, 166A. Venation, upper surface: 172A. Venation, lower surface: 184D. Petiole: 148B.

Flower description:

*Appearance.*—Single rounded star-shaped flat flowers with five petals. Flowers face upright to outwardly. Flowers positioned about 3 cm to 4 cm above the foliar plane.

*Natural flowering season.*—Long flowering period, from early summer through the fall in Scotland, United Kingdom; flowering continuous during this period. Flowers not persistent.

*Fragrance.*—None detected.

*Flower longevity.*—About one week.

*Flower diameter.*—About 1.5 cm to 2 cm.

*Flower depth.*—About 5 mm to 10 mm.

*Flower buds.*—Length: About 5 mm. Diameter: About 3 mm. Shape: Ovoid. Texture: Pubescent. Color: 148B.

*Petals.*—Length: About 1.5 cm. Width: About 1 cm. Shape: Broadly spatulate; recurved towards the apex. Apex: Emarginate. Base: Attenuate. Margin: Entire; undulate. Texture, upper and lower surfaces: Smooth. Color: When opening and fully opened, upper surface: 81B; throat, 155C with nectar guides, 81B. When opening and fully opened, lower surface: 81D; towards the base, 155C with nectar guides, 81B.

*Sepals.*—Quantity: Five. Length: About 7 mm. Width: About 4 mm. Shape: Elliptic; apex, aristate; base, fused. Texture, upper and lower surfaces: Smooth. Color, upper and lower surfaces: 148A.

*Peduncle.*—Length: About 2.5 cm to 4 cm. Diameter: About 1 mm. Strength: Moderately strong. Texture: Pubescent. Color: 148B.

*Reproductive organs.*—Stamens: Quantity per flower: Ten arranged in two whorls. Filament length: About 5 mm. Anther shape: Oblong, curved. Anther color: 159A. Pollen amount: None observed. Pistils: Quantity per flower: One, five-parted. Pistil length: About 5 mm. Stigma color: 84A. Ovary color: 138D densely covered with white hairs.

*Seed description.*—Seed development has not been observed.

Disease/pest resistance: Plants of the new *Geranium* have not been noted to be resistant to pathogens and pests common to *Geranium.*

Garden performance: Plants of the new *Geranium* have been observed to have excellent garden performance and to tolerate wind and rain. Plants of the new *Geranium* have been observed to be tolerate temperatures from about 2° C. to about 30° C.

It is claimed:

1. A new and distinct cultivar of *Geranium* plant named 'Tanya Rendall', as illustrated and described.

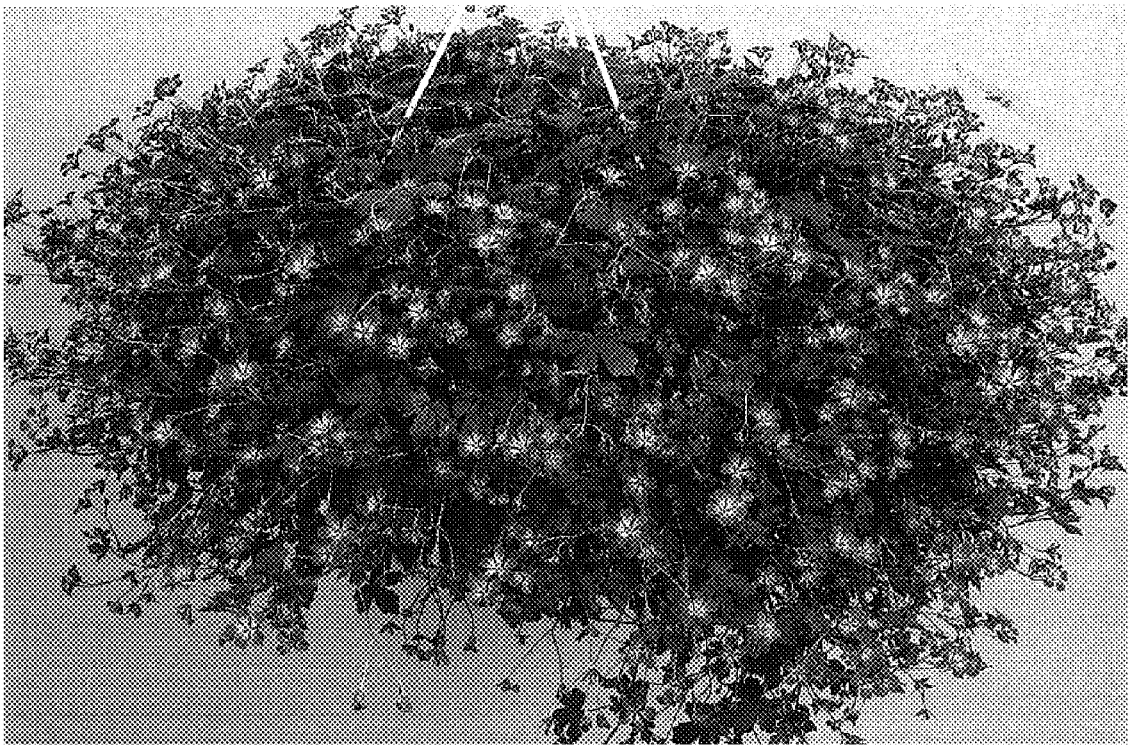

* * * * *